United States Patent [19]

Jones

[11] E Patent Number: Re. 32,964

[45] Reissued Date of Patent: Jun. 27, 1989

[54] SYSTEM FOR MEASURING THE PORE VOLUME AND PERMEABILITY OF VERY TIGHT CORE PLUGS AND METHOD THEREFOR

[75] Inventor: Stanley C. Jones, Littleton, Colo.

[73] Assignee: Marathon Oil Company, Findlay, Ohio

[21] Appl. No.: 101,239

[22] Filed: Sep. 25, 1987

Related U.S. Patent Documents

Reissue of:

[64] Patent No.: 4,627,270
Issued: Dec. 9, 1986
Appl. No.: 816,608
Filed: Jan. 6, 1986

[51] Int. Cl.[4] ..... G01N 15/08

[52] U.S. Cl. ..... 73/38

[58] Field of Search ..... 73/38

[56] References Cited

U.S. PATENT DOCUMENTS

| | | | |
|---|---|---|---|
| 2,705,418 | 4/1955 | Reichertz et al. | 73/38 |
| 2,821,680 | 1/1958 | Slusser et al. | 73/38 X |
| 3,420,093 | 1/1969 | Collins | 73/38 |
| 3,839,899 | 10/1974 | McMillen | 73/38 |

*Primary Examiner*—Michael J. Tokar
*Assistant Examiner*—Joseph W. Roskos
*Attorney, Agent, or Firm*—Jack L. Hummel; Rodney F. Brown

[57] ABSTRACT

A system and method for measuring Klinkenberg permeability and pore volume of a tight core plug sample is provided wherein a pressure transducer is positioned between the sample cell and the manifold of the system.

7 Claims, 3 Drawing Sheets

SYSTEM FOR MEASURING THE PORE VOLUME AND PERMEABILITY OF VERY TIGHT CORE PLUGS AND METHOD THEREFOR

Matter enclosed in heavy brackets [ ] appears in the original patent but forms no part of this reissue specification; matter printed in italics indicates the additions made by reissue.

BACKGROUND OF THE INVENTION

1. Technical Field

The present invention relates to a system and method for measuring permeability and pore volume of core samples and, in particular, to an automated system and method therefore for measuring Klinkenberg permeability and pore volume of very tight oil core samples (i.e., permeability of less than one-hundred microdarcies).

2. [Description of the Related Art] *Discussion of Prior Art*

In FIG. 1, is the conventional schematic diagram of a helium flow system in an automated Klinkenberg [permeameter/porosimeter] *permeameter/prorsimeter*. The apparatus shown in FIG. 1 includes a helium reservoir 10 containing a small helium tank 20 and a large helium tank 30, a manifold 40, a pressure transducer 50, and a core sample holder 60. Valve 80 connects the small helium tank 20 to the manifold 40 over lines 82 and 84. Valve 90 connects the large helium tank 30 over lines 92 and 94 to the manifold 40. The helium that is delivered through valve 130 flows through lines 132 and 134. The vent valve 100 is in fluid communication over lines 102 and 104 with the manifold 40 and the manifold 40 is further connected with the sample holder 60 over lines 112 and 114 through valve 110. Finally, the pressure transducer 50 is connected to the manifold 40 over line 52. Contained within the sample holder 60 is a core plug 70. A poppet valve 120 releases gas to atmosphere as shown.

In conventional operation, the core plug 70 is mounted into a sample holder 60. The core plug 70 is subjected to atmospheric pressure by opening vent valve 100, valve 110, and poppet valve 120. After a period of time, pressure within the core plug 70 reaches equilibrium with atmospheric pressure at zero psig. After reaching atmospheric pressure equilibrium, valves 100, 110, and 120 are closed. The manifold 40 is then pressurized with helium gas by opening fill valve 130 and the manifold is pressurized with helium to a typical valve of 250 psig. The pressure in the manifold 40 is monitored by transducer 50. At the desired pressurization, valve 130 is closed. For a period of time, such as a few seconds, the manifold pressure is allowed to stabilize and the pressure in the transducer is recorded.

The system is now ready for testing. Valve 110 is opened and the pressurized helium in manifold 40 is expanded into the sample holder 60 and into the core plug 70. This is further explained by reference to FIG. 2. In FIG. 2, the initial pressurization of the manifold 40 is termed $P_{FILL}$. At time $t_1$, valve 110 is opened and the pressure decreases, in a nonlinear fashion, to an equilibrium pressure, $P_E$ at time $t_2$. Curve 200 represents the change in pressure due to the increase in volume by adding the volumes from the sample holder 60, i.e., (a) the volume below valve 110 and above the upper surface 400 of core plug 70 and below the sample 70 and above valve 120 is termed the dead volume and (b) within the core plug 70 is termed the pore volume.

FIG. 2 illustrates the pressure-time behavior for four different cases. Curves 210 and 210a depict the approach to pressure equilibrium, $P_{Ea}$, for two core plugs having identical pore volumes, but having differing permeability. The plug corresponding to core 210a has a higher permeability than the 210 plug, hence pressure equilibrium is reached more rapidly in the plug for curve 210a. Curves 200 and 200a correspond to core plugs with identical pore volumes, but having volumes which are higher than those depicted by curves 210 and 210a. The higher pore volume allows more gas expansion, which results in a lower equilibrium pressure, $P_E$. Again, the permeability of the plug represented by curve 200a is higher than that represented by curve 200. Consequently, pressure equilibrium occurs more quickly for plugs having curve 200a than for plugs having curve 200.

Hence, under conventional approaches, when there is no further change of pressure with respect to time, equilibrium has been reached and the pore volume of the core plug 70 can be calculated based on the ratios of the initial pressure $P_{FILL}$ the equilibrium pressure $P_E$, and further based upon the known manifold and dead volumes.

For example, if the manifold volume, $V_o$, is 20.277 cubic centimeters, the dead volume, $V_d$, is 4.238 cubic centimeters, $P_{FILL}$ at time $t_1$ is 238.12 psig, and $P_E$ at time [t2] $t_2$ is 162.56 psig, then, the pore volume, $V_p$ can be approximately calculated as:

$$\begin{aligned} V_P &= V_o(P_{FILL}/P_E) - 1) - V_d \\ &= 20.277(238.12/162.56 - 1) - 4.238 \\ &= 5.187 \text{ cubic centimeters} \end{aligned} \qquad \text{(Formula 1)}$$

There are several drawbacks to the conventional approach for measuring permeability and pore volumes in low permeability (very tight) core plugs (i.e., having a permeability of several microdarcies). Such core samples take longer times ($t_1$ and $t_2$) to reach the equilibrium pressures of atmosphere pressure initially in the core plug and $P_E$ and, therefore, the conventional approach is time consuming. Secondly, for any core plug and especially for very tight core plugs, there is no determination (i.e., no way of monitoring) of whether or not the pressure within the plug has truly reached atmospheric pressure, which may take several minutes to an hour or more to obtain. The present invention, as will be explained in the following, eliminates those two major drawbacks and provides a quicker and more accurate determination of pore volume and a quicker determination of permeability for very tight core plugs.

DISCLOSURE OF THE INVENTION

Two problems, faced in current systems and methods for measuring Klinkenberg permeability and pore volume of very tight core samples is (a) the determination of whether the core sample has obtained atmospheric pressure prior to testing and (b) is the length of time that it takes to conduct these tests. The improved permeability/pore volume system and method of the present invention provides a solution to these problems by first changing the location of the pressure transducer 50 from the manifold to a point between valve 110 and the sample holder 60.

To measure the pore volume of a core plug, the manifold volume, dead volume, and pore volume are pressurized to a predetermined pressure, $P_{FILL}$. After several seconds, valve 110 is closed and the pressure in the transducer, dead volume and pore volume is allowed to come to a first equilibrium. In the meantime, the manifold is vented to atmospheric pressure to obtain zero psig. After the first pressure equilibrium has been obtained, the manifold is sealed and valve 110 is opened, allowing the pressurized gas below valve 110 to expand into the manifold and a second equilibrium pressure is measured. The pore volume is determined from the two measured equilibrium pressures. The system and method of the present invention provides greater accuracy and speed.

The Klinkenberg permeability of a tight core plug is measured in the same manner as in the prior art automated Klinkenberg permeameter/porosimeter. However, in the present invention, because the transducer is located below valve 110, this valve can be closed during the permeability measurement. The reduced-volume helium reservoir, which comprises the volume within the transducer and in the lines between valve 110 and the upper face of the core plug, causes a proportional decrease in the time required to make the permeability measurement compared to the time required if the manifold volume were also included in the helium reservoir volume - as it is in the prior art design. Thus the system of the present invention also increases the speed of permeability measurements in tight core plugs.

BEST MODE FOR CARRYING OUT THE INVENTION

Figure 1:
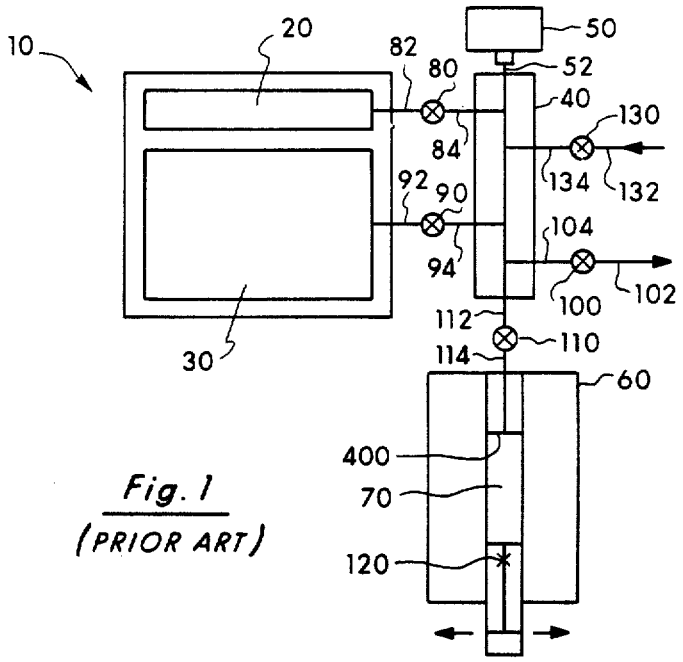
Fig. 1 (PRIOR ART)
FIG. 1 sets forth a prior art device for measuring permeability and pore volume of oil reservoir core samples.
Figure 4:
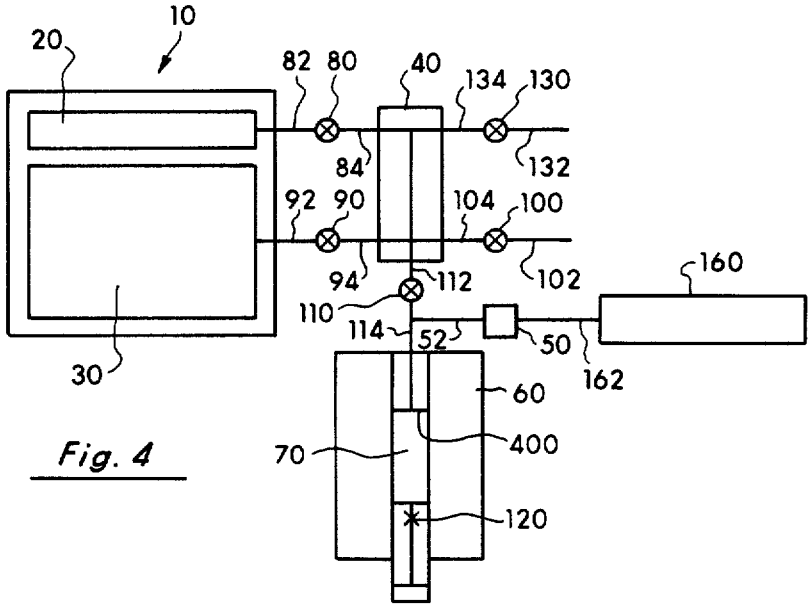
FIG. 4 is a block diagram of the permeability/pore volume system of the present invention.

A preferred modification of the prior art apparatus of FIG. 1, which can be used in the method of the present invention, is set forth in FIG. 4. Where possible, like references refer to like items between FIGS. 1 and 4.

Specifically, in the modification, as shown in FIG. 4, the manifold 40 of FIG. 1 has been designed to have a smaller volume. Pressure transducer 50 has been removed from manifold 40 and has been attached to the line 114 below valve 110.

In the embodiment of FIG. 4, manifold 40 is constructed so that its volume is approximately 5 to 10 cubic centimeters and the "valve 110-transducer 50-core holder 60" assembly is constructed so that the dead volume (i.e., from the lower portion of valve 110 to the upper face 400 of the core plug 70 and into the transducer 50 and from the bottom of the core sample to the poppet valve 120) is approximately 3 to 4 cubic centimeters. In comparison to the arrangement of FIG. 1, the manifold volume, $V_o$, down to valve 110 of FIG. 1 including the volume into transducer 50 is typically about 20 cubic centimeters and the dead volume, $V_d$, is about 4 to 5 cubic centimeters. The ratio of $V_o$ to $V_d$ in the prior art approach of FIG. 1 is about 4:1 or 5:1 whereas the ratio of $V_o$ to $V_d$ in the preferred embodiment of FIG. 4 is 2:1 or 3:1.

With reference to FIG. 4, the operation of the present invention occurs as follows for pore volume measurements. Poppet valve 120 is closed, valve 110 is opened, valve 100 is closed, and valve 130 is opened to allow the manifold 40 and the sample holder 60 to become pressurized to approximately 250 psig [of] *or* $P_{FILL}$ for a period of time from several seconds to one or two minutes. During this time, the core plug 70 will also become partially pressurized. Then, valves 130 and 110 are closed. The pressure transducer 50 is monitored until the pressure reaches equilibrium. This pressure [$P_{E1}$] *PE1* is then recorded.

During the period when the pressure in the core plug is approaching [PE1] $P_{E1}$ equilibrium, valve 100 is opened venting the manifold 40 to atmosphere. In a second or more, the manifold quickly reaches zero psig, then valve 100 is closed. After pressure equilibrium, [PE1] $P_{E1}$, has been achieved valve 100 is reopened so that the pressurized helium in the sample holder 60 and core plug 70 is allowed to expand back into manifold 40. Eventually, after a period of time, the helium gas in the manifold 40, the sample holder 60, and the core plug 70, will reach a second equilibrium pressure, $P_{E2}$.

Figure 3:
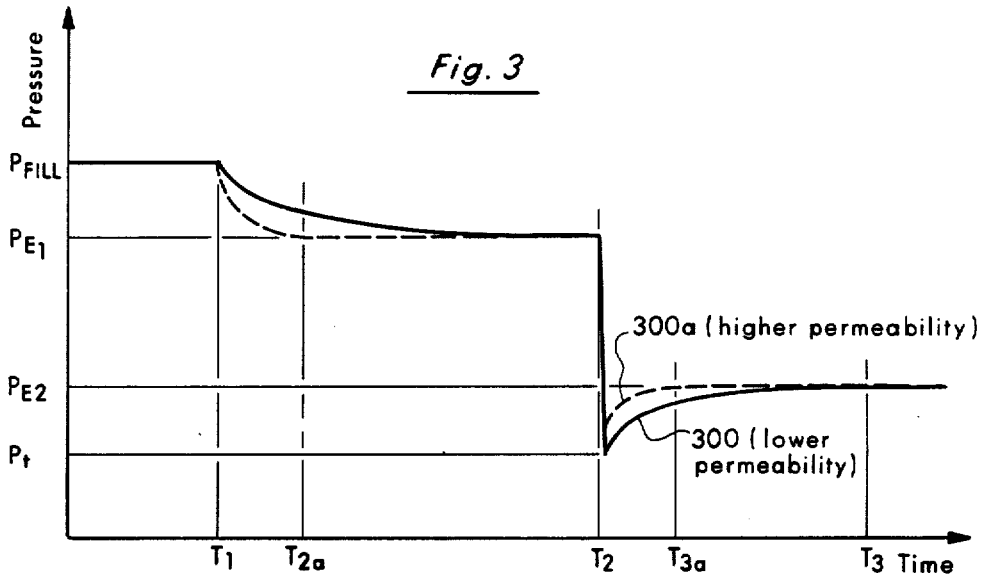
FIG. 3 is a graphical illustration showing the pressure changes and the operation of the improved permeability/pore volume system of the present invention as shown in FIG. 4.

This is illustrated in the graph of FIG. 3 wherein $P_{FILL}$ is the initial pressure to which the manifold 40 and pressure transducer 50 are charged. The core plug is also subjected to this pressure, but because of its very low permeability the core plug does not become fully pressurized throughout its entire length. At time $T_1$, valves 110 and 130 are closed, after which time the volume of gas contained in line 114 down to the core face 400 (i.e., the dead volume) and the gas in the core plug 70 and in the volume below it, to valve 120, gradually reaches pressure equilibrium, $P_{E1}$ at time $T_2$, after which there is no further change in pressure. Before time $T_2$, the manifold 40 is vented to atmospheric pressure by opening valve 100 for several seconds and then closing it. At time $T_2$, pressure $P_{E1}$ sensed by transducer 50 is recorded and then valve 110 is openend. Gas from lines 114 and 52, and from transducer 50 above core face 400 quickly expands into manifold 40, causing a sudden decrease in pressure to pressure $P_f$. Gas from the core plug and the volume below if flow more slowly into the manifold 40 and into pressure transducer 50, causing a gradual pressure build-up until equilibrium pressure, $P_{E2}$ is achieved at time $T_3$, after which time no further pressure change occurs.

Hence, under the teachings of the present invention, both $P_{E1}$ and $P_{E2}$ are pressures that are recorded and delivered over lines 162 to a suitable device 160 such as a computer for ascertaining the pore volume. It is to be expressly understood that device 160 is further capable of controlling the operation of valves 80, 90, 100, 110, 120, and 130 over suitable connections not shown in FIG. 4. Based upon the ratios of the two pressures, the pore volume of the core plug 70 can be ascertained. The curve 300 of FIG. 3 represents the solid curve for a very tight core plug whereas the dashed line curve 300a represents a curve for a core plug of higher permeability, but having the same pore volume as the plug represented by curve 300. In typical embodiments, pressure $P_{E1}$ is 180 to 240 psig and pressure $P_{E2}$ is between 90 to 120 psig. It is desirable to keep the equilibrium pressures in this range as will be explained more fully in the following.

The time to reach equilibrium is approximately proportional to the compressibility of the fluid used. For example, and in way of illustration, suppose the manifold 40 were filled with water at 250 psig, and the core plug were filled with water at zero psig. Because water has such a low compressibility, only a fraction of a drop flowing from the manifold into the core plug would equalize the pressures in both. If the fluid were instead a gas at low pressure, considerable volumetric flow from manifold 40 must take place into the core plug 70 in order to obtain pressure equilibrium.

Figure 2:
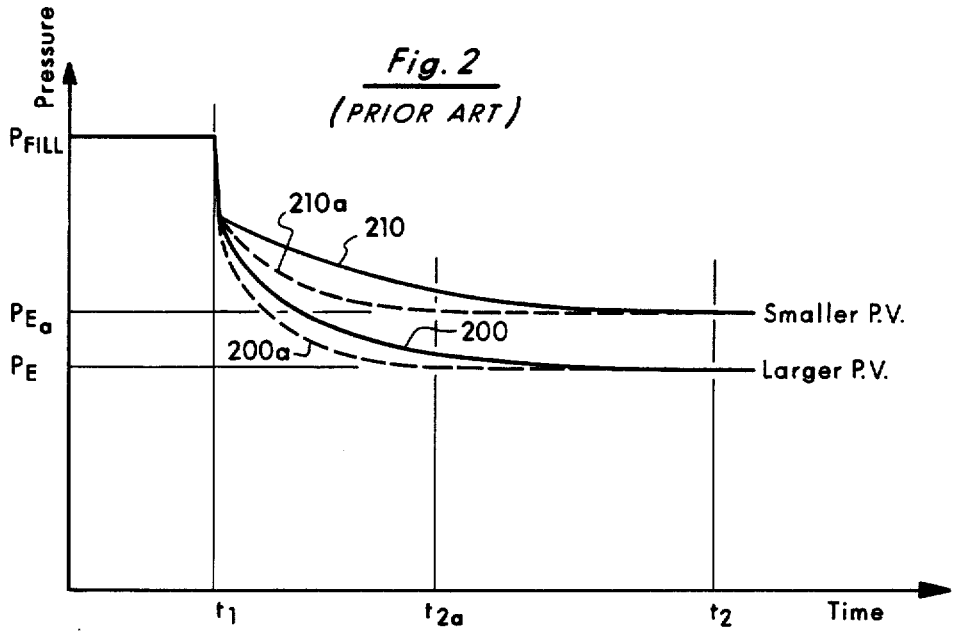
Fig. 2 (PRIOR ART)
FIG. 2 is a graphical illustration of the operation of the prior art system shown in FIG. 1.

Less time is required to reach the initial pressure equilibrium, $P_{E1}$, when the teachings of the present invention are followed, compared to the methods of the prior art as shown in FIGS. 1 and 2. The initial equilibrium pressure for a pore volume measurement, according to the prior art, is zero psig, whereas it is preferably 180 to 240 psig according to the present invention. The higher pressures result in a thirteen-fold to seventeen-fold reduction in the gas compressibility over that performed in prior art and a corresponding reduction in time to reach equilibrium.

In the present invention, the second equilibrium pressure, $P_{E2}$, according to FIG. 3, is somewhat lower than the corresponding equilibrium pressure, $P_E$, of the prior art (see FIG. 2). This causes a higher gas compressibility and would require a longer equilibrium time were it not for the smaller manifold volume of the present invention. The time required to achieve this second equilibrium should be about half that required in the prior art. Thus, the time saved for both equilibria involved in a pore volume measurement under the teachings of the present invention is considerable.

There is another important benefit found in the configuration of FIG. 4. An absolutely leak-free system is required to obtain accurate pore volume measurements. Leaks are difficult to ascertain in the prior art configuration of FIG. 1. The approach to equilibrium (see FIG. 2) is accompanied by a declining pressure. One cannot easily tell whether the decline is due to helium diffusing into the core plug or due to a leak in the system. Both would cause the pressure to decline. On the other hand, the approach to the final equilibrium, $P_{E2}$, as shown in FIG. 3 for the configuration of the present invention is achieved with an increasing pressure as helium diffuses from the plug, which is at a higher pressure than the manifold. If a leak is present, then the pressure rise will be followed by a decline; i.e., the pressure will pass through a maximum with time.

The configuration of FIG. 4 offers yet another benefit. The time required for measuring the permeability of very tight core plugs is reduced. To accomplish a permeability measurement, poppet valve 120 is closed as is valve 100. The manifold 40 and the core plug 70 are pressurized to about 240 psig with helium by opening valve 130. After a few seconds, valve 130 is closed and valve 120 is opened, allowing helium that exits from the core plug to be vented to atmospheric pressure. Permeability can be calculated from the instantaneous time rate of pressure decay based upon a number of measurements under methods that are well known; e.g., Jones, S. C., "A Rapid Accurate Unsteady-State Klinkenberg Permeameter", Soc. of Petroleum Engineers, J., ([Oct.] *October* 1972), 383–397.

This rate of pressure decay is directly proportional to the volume of the manifold 40, lines 112 and 114 and pressure transducer 50 up to the upper core face 400. Because this volume is reduced, in the configuration of FIG. 4, by a factor of 2 to 2.5 from that taught in the prior art, so, too, is the time for a permeability measurement reduced by a factor of 2.0 to 2.5.

A further time reduction can be made in measuring the permeability of an extremely tight plug, i.e., less than about 0.1 md. To accomplish this, the core is charged with helium to pressure $P_{FILL}$ as before. But now, before poppet valve 120 is opened to start the pressure decay, valve 110 is closed, leaving only the volume below valve 110 as the helium reservoir to be delivered through opened valve 110. This results in approximately a eight-fold time decrease from the prior art configuration. This is made possible because the pressure transducer is now connected below valve 110, and can monitor the pressure decay when valve 110 is closed.

In measuring high permeability plugs (i.e., greater than 50 or 75 md.), one or both helium tanks 20, 30 are charged with helium as taught in the prior art by selectively opening valves 80 and 90 and this feature is also implemented in the present invention.

In making pore volume measurements, an error analysis shows that the maximum accuracy is obtained when: (1) pressure $P_{E1}$ is as close as practicable to the full-scale reading of the pressure transducer, which, in the preferred embodiment, is 250 psig, (2) pressure $P_{E2}$ is about one-half the value of pressure $P_{E1}$, and (3) the dead volume, $V_d$, i.e., the volume in sample holder 60 above and below core plug 70 and below valve 110 and above valve 120 is as small as possible. The minimum practical dead volume under the teachings of the present invention, without severely restricting the flow paths to and from the core, is about 3 to 4 cubic centimeters. The second requirement under the teachings of the present invention sets the most desirable manifold volume, $V_o$. It should be equal to the sum of the core's pore volume $V_p$ and the dead volume $V_d$. If the dead volume, $V_d$, is 3 to 4 cubic centimeters and typical pore volumes, $V_p$, range from 2 to 8 cubic centimeters, then the manifold volume, $V_o$, should fall in the range of 5 to 10 cubic centimeters. The lower end of this range is favored because the maximum accuracy is desired for plugs having the smallest pore volume. Here, a given error in the absolute measurement causes the largest percentage error. The smaller manifold volume is also desired because it results in a higher $P_{E2}$ than would a larger volume. Hence, the time to reach equilibrium is reduced.

Figure 5:
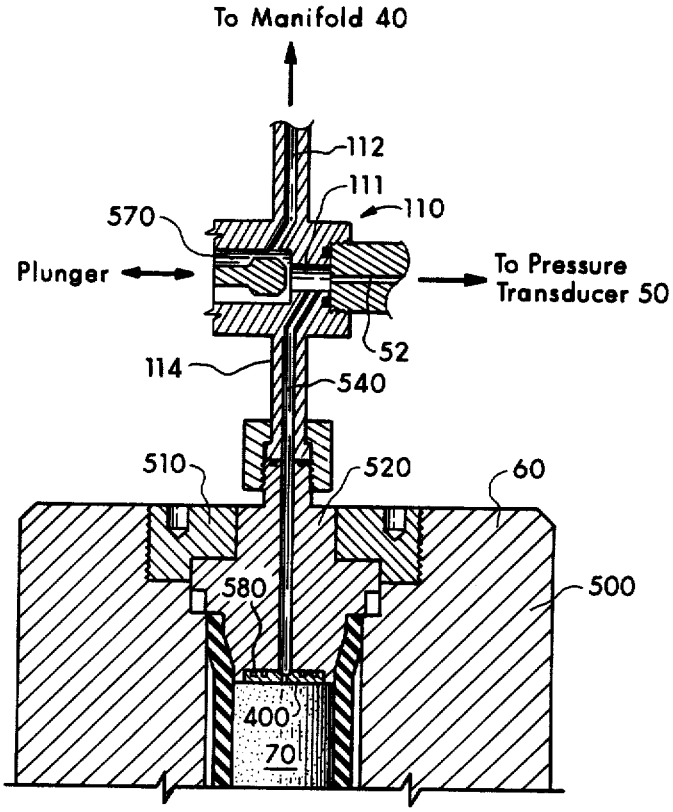
FIG. 5 is the cross-sectional representation of the volume in the region of the core sample and the pressure transducer.

In FIG. 5, a core sample holder 60 is set forth which corresponds to the type of core sample holder disclosed in [co-pending patent application Ser. No. 06/651,558] *U.S. Pat. No. 4,573,342 which issued March 4, 1986.* Sample holder 60 has a main body 500 with a top cap 510 firmly holding a connector portion 520. The conduit 114 connects to the valve 110 so that a fluid path 540 is provided from the valve 110 to the sample holder 60. The fluid path 112 is established from the valve 110 to the manifold 40 and a fluid path 52 is established to the pressure transducer 50. The valve 110 works in a conventional fashion through actuation of a plunger 570 to open and close a fluid path between fluid paths 940 and 112. Such a valve may be modified from a conventional valve of the type manufactured by Nupro Company, 4800 E. 345th Street, Wilboughby, Ohio 44094 as Model SS-4BK-V51-1C. The modification consists of counterboring and tapping the bottom of the valve to accommodate the fitting that leads to transducer 50, and of providing an O-ring seal therefore. Fluid path 540 accesses a perforated plate 580 and then the upper surface 400 of sample core 70.

FIG. 5 is intended to be only an example of one way to achieve the flow configuration shown in FIG. 4. Several variations are possible under the below described formulas; for example, a compact arrangement can be configured by incorporating valves 80, 90, 130, 100, and 110 into the manifold body itself by drilling appropriate holes in the manifold to accommodate the air-operated valve stems. Several seals are also eliminated when these valves as well as helium tanks 20 and 30 are integrated into the manifold block.

Hence, upon inspection of FIG. 5, the volume, [Vb] $V_b$, equals the volume of the transducer along path 52 plus the volume of the line 114 plus the volume of the perforated plate 580 plus the volume of the cavity 111 beneath the valve plunger when it is in the closed position. And, the lower volume, [Vd] $V_d$, equals volume, [Vb] $V_b$, plus the volume at the bottom of the plug 70 and valve 120. Hence, the following formulas:

$$V_b = V(TRANSDUCER) + V(LINE) + V(PLATE) + V(CAVITY) \quad \text{(Formula 2)}$$

$$V_d = [V_b]\ Vb + V(\text{Bottom}) \quad \text{(Formula 3)}$$

In the preferred embodiment, the total volume $V_d$ is designed to be typically 3 to 4 cubic centimeters.

The upper volume $V_o$ is equal to the volume of the manifold 40, the volume of the line 112 and the volume to the valves 130, 100, and their associated lines. Hence, the upper volume can be expressed as:

$$V_o = V(\text{MANIFOLD}) + V(\text{IN VALVES } \mathbf{80, 90, 100, \text{ and } 130}) + V(\text{LINES } \mathbf{84, 94, 104, \text{ and } 134}) \quad \text{(Formula 4)}$$

In an ideal situation, under the teachings of the present invention, the upper volume $V_o$ should equal the lower volume $V_d$ plus the pore volume of the core plug [VP] $V_p$ as set forth in Formula 3:

$$V_o = V_d + V_p \quad \text{(Formula 5)}$$

In the construction of the permeability/porosity apparatus of the present invention, valves 100, 130, 110 and the associated lines, the manifold 40, the pressure transducer 50 and the sample holder 60 are all designed to be within the ranges provided by Formulas 2 through 4. It is to be understood that when the plunger 570 opens, a displacement of about 0.1 to 0.3 cubic centimeters occurs, and that this plunger displacement can be accounted for. The embodiment of FIG. 4 is desirable over that shown in FIG. 1 since monitoring of the pressure by pressure transducer 50 is located near and is in fluid communication with the core plug 70. Furthermore, since equilibrium time is inversely proportional to compressibility of the helium gas, the embodiment shown in FIG. 4 is several times faster than conventional pore volume measurements. Finally, in the prior art embodiment of FIG. 1, the smallest available reservoir volume for the measurement of permeability was the combination of both the upper and lower volumes, $V_o$ plus $V_b$ or typically 25 cubic centimeters. Under the teachings of the present invention, the smallest is [Vb] $V_b$ or 3 to 4 cubic centimeters. This relationship provides a factor of at least six times in speed up of measurement for permeability. For example, under the conventional approach shown in FIG. 1, typically if 45 minutes passed for a permeability measurement, now under the embodiment shown in FIG. 6, only six or seven minutes would pass. Hence, for very tight core plugs a definite speed up occurs.

Although the system and method of the present invention has been specifically set forth in the above disclosure, it is to be understood that modifications and variations can be made thereto which will still fall within the scope and coverage of the following claims.

I claim:

1. A method for determining the pore volume of *a* very tight core [samples] *sample* with an apparatus having a manifold in selective fluid communication with a sample holder holding said core sample, said sample holder having an outlet, said method comprising the steps of:

(a) sealing the outlet of the sample holder *while maintaining the sample holder in fluid communication with the manifold*, (b) pressurizing the manifold [volume] and the sample holder with a gas to a predetermined pressure, $P_{FILL}$, (c) sealing the [core] *sample* holder and *a* pressure transducer from the manifold *while maintaining the pressure transducer in fluid communication with the sample holder*, (d) waiting for the gas pressure in the [core] *sample* holder to reach a first equilibrium [state] *pressure*, $P_{E1}$, (e) measuring the value of *said* pressure $P_{E1}$ *with the pressure transducer at a location between the manifold and the sample holder*, (f) venting the manifold to *the* atmosphere so that the manifold [pressure obtains zero psig] *is at atmospheric pressure*, (g) sealing the manifold in response to said venting so that the sealed manifold [contains zero psig] *remains at atmospheric pressure*, (h) delivering the pressurized gas at said first equilibrium pressure, $P_{E1}$, from the sample holder into the manifold *such that the sample holder, manifold and pressure transducer are in fluid communication with one another*, (i) waiting for the delivered pressurized gas to reach a second equilibrium [state] *pressure*, $P_{E2}$, (j) measuring the value of *said* pressure [PE2] $P_{E2}$ with the pressure transducer at the aforesaid location, and (k) determining the pore volume, [Vp] $V_p$, of the core [plug] *sample* in the sample holder based upon the measured values of *said first and second equilibrium* pressures, $P_{E1}$ and $P_{E2}$.

2. A method for determining the pore volume of *a* very tight core [samples] *sample* with an apparatus having a manifold in selective fluid communication with a sample holder holding said core sample, said sample holder having an outlet, said method comprising the steps of:

(a) providing a manifold volume, $V_o$, that is substantially equal to the pore volume, $V_p$, plus the dead volume[, $V_d$,] of [the line and] the sample holder *and a line between the manifold and the sample holder, $V_d$*, (FORMULA 5), (b) sealing the outlet of the sample holder *while maintaining the sample holder in fluid communication with the manifold,*

(c) pressurizing the manifold [volume] and the sample [holders] *holder with a* gas to a predetermined pressure, $P_{FILL}$, (d) sealing the [core] *sample* holder and *a* pressure transducer from the manifold *while maintaining the pressure transducer in fluid communication with the sample holder,*

(e) waiting for the gas pressure in the [core] *sample* holder to reach a first equilibrium [state] *pressure,* $P_{E1}$, (f) measuring the value of *said* pressure $P_{E1}$ *with the pressure transducer,*

(g) venting the manifold to *the* atmosphere so that the manifold [pressure obtains zero psig] *is at atmospheric pressure,*

(h) sealing the manifold in response to said venting so that the sealed manifold [contains zero psig] *remains at atmospheric pressure,*

(i) delivering the pressurized gas at pressure, $P_{E1}$, from the sample holder into the manifold *such that the sample holder, manifold and pressure transducer are in fluid communication with one another,*

(j) waiting for the delivered pressurized gas to reach a second equilibrium [state] *pressure,* $P_{E2}$, (k) measuring the value of *said* pressure, $P_{E2}$, *with the pressure transducer,* and (l) determining the pore volume, $V_p$, of the core [plug] *sample* in the sample holder based upon the measured values of *said first and second equilibrium* pressures, $P_{E1}$ and $P_{E2}$.

3. A method for determining the pore volume of *a* very tight core [samples] *sample* with an apparatus having a manifold in selective fluid communication with a sample holder holding said core sample, said sample holder having an outlet, said method comprising the steps of:

(a) providing a manifold volume, $V_o$, that is substantially equal to the pore volume, $V_p$, plus the dead volume[, $V_d$,] of the [line and the] sample holder *and a line between the manifold and the sample holder,* $V_d$, (FORMULA 5), (b) sealing the outlet of the sample holder *while maintaining the sample holder in fluid communication with the manifold,*

(c) pressurizing the manifold [volume] and the sample [holders] *holder* with a gas to a predetermined pressure, $P_{FILL}$, (d) sealing the [core] *sample* holder and *a* pressure transducer from the manifold *while maintaining the pressure transducer in fluid communication with the sample holder,*

(e) measuring the value of [the] *a* first equilibrium pressure, $P_{E1}$, *with the pressure transducer* at a location [above] *on said line between* the [core] sample *holder* and [below] the manifold, (f) venting the manifold to *the* atmosphere so that the manifold [pressure obtains zero psig] *is at atmospheric pressure,*

(g) sealing the manifold in response to said venting so that the sealed manifold [contains zero psig] *remains at atmospheric pressure,*

(h) delivering the pressurized gas at *said first equilibrium* pressure, $P_{E1}$, from the sample holder into the manifold *such that the sample holder, manifold and pressure transducer are in fluid communication with one another,*

(i) measuring the value of a second equilibrium pressure, $P_{E2}$, *with the pressure transducer* at the aforesaid location, and (j) determining the pore volume, $V_p$, of the core [plug] *sample* in the sample holder based upon the measured values of *the first and second equilibrium* pressures, $P_{E1}$ and $P_{E2}$.

4. An improved apparatus for determining the pore volume of *a* very tight core [samples] *sample,* said apparatus having a manifold (40) in selective fluid communication through [a line] *lines* (112, 114) with a sample holder (60) holding said core sample (70), said sample holder (60) further having an outlet valve (120) being capable of being opened to atmospheric pressure, said improved apparatus comprising:

a valve (110) connected to said [line] *lines* (112, 114) for selectively opening and closing said [line] *lines* (112, 114), a transducer (50) connected to said line ([112,] 114) at a location [below] *between* said valve (110) *and said sample holder* (60), said manifold (40) being formed to have a volume, $V_o$, substantially equal to the pore volume, [Vp] $V_p$, of said core sample plus [the] *a* dead volume[, $V_d$,] of said line (114) [below said valve (110)], said sample holder (60), and *a* line (52) to said transducer (50), $V_d$, means (130, 132, 134) for delivering gas into said manifold (40) and sample holder (60) at a fill pressure, $P_{FILL}$, when said valve (120) is closed, said transducer (50) being capable of ascertaining a first equilibrium pressure, $P_{E1}$, when said valve (110) is closed, means (100, 102, and 104) for venting gas into the atmosphere from said manifold (40) when said valve (110) is closed in response to said ascertainment of said first equilibrium pressure, said venting means becoming closed when said manifold (40) obtains zero psig, said transducer (50) being capable of ascertaining a second equilibrium pressure, $P_{E2}$, when said valve (110) is opened, and means (160) connected to said transducer (50) for determining *the pore volume of the core sample from* said first and second equilibrium pressures, $P_{E1}$ and $P_{E2}$.

5. A method for determining the permeability of *an* extremely tight core [samples] *sample* with an apparatus having a manifold in selective fluid communication with a sample holder holding [a] said core [plug] *sample,* said sample holder having an outlet, said method comprising the steps of:

(a) closing the outlet of the sample holder, (b) pressurizing the manifold [volume] and [core] *the sample* holder with a gas to a predetermined pressure, $P_{FILL}$, (c) selectively sealing the manifold from the [core] *sample* holder, (d) opening the outlet of the sample holder [in order to obtain atmospheric pressure] *to the atmosphere,*

(e) allowing the pressure $P_{FILL}$ *in the sample holder* to decay *to atmospheric pressure* as the gas flows from [the] *a* volume at the seal [above] *between* the [core] *sample* holder *and the manifold* through the core [plug] *sample,* and through the outlet,

[thereby venting the gas to atmospheric pressure,]

(f) measuring a predetermined number of [values, in time, of the] instantaneous pressure *values over time* near said seal during the [period of] pressure decay, and (g) determining the permeability of the core [plug] *sample* from said instantaneous [time and] pressure [measurements] *values over time.*

*6. The method of claim 2 wherein the sample holder and pressure transducer are sealed from the manifold by sealing the line therebetween.*

*7. The method of claim 3 wherein the sample holder and pressure transducer are sealed from the manifold by sealing the line therebetween.*

* * * * *

UNITED STATES PATENT AND TRADEMARK OFFICE

CERTIFICATE OF CORRECTION

PATENT NO. : RE 32,964

DATED : June 27, 1989

INVENTOR(S) : Stanley C. Jones

It is certified that error appears in the above-identified patent and that said Letters Patent is hereby corrected as shown below:

| | |
|---|---|
| Col. 1, lines 23 and 24: | Delete "[permeameter/porosimeter] permeameter/ prorsimeter" and insert --permeameter/ porosimeter--. |
| Col. 1, line 51: | Delete "valve" and insert --value--. |
| Col. 4, lines 17 and 18: | Delete "[$P_{E1}$] PE1" and insert --$P_{E1}$--. |
| Col. 4, line 45: | Delete "openend" and insert --opened--. |
| Col. 4, line 49: | Delete "if" and insert --it--. |
| Col. 7, line 28: | Delete "[$V_b$] Vb" and insert --$V_b$--. |

Signed and Sealed this

Fifteenth Day of May, 1990

*Attest:*

*Attesting Officer*

HARRY F. MANBECK, JR.

*Commissioner of Patents and Trademarks*